Figure 1:
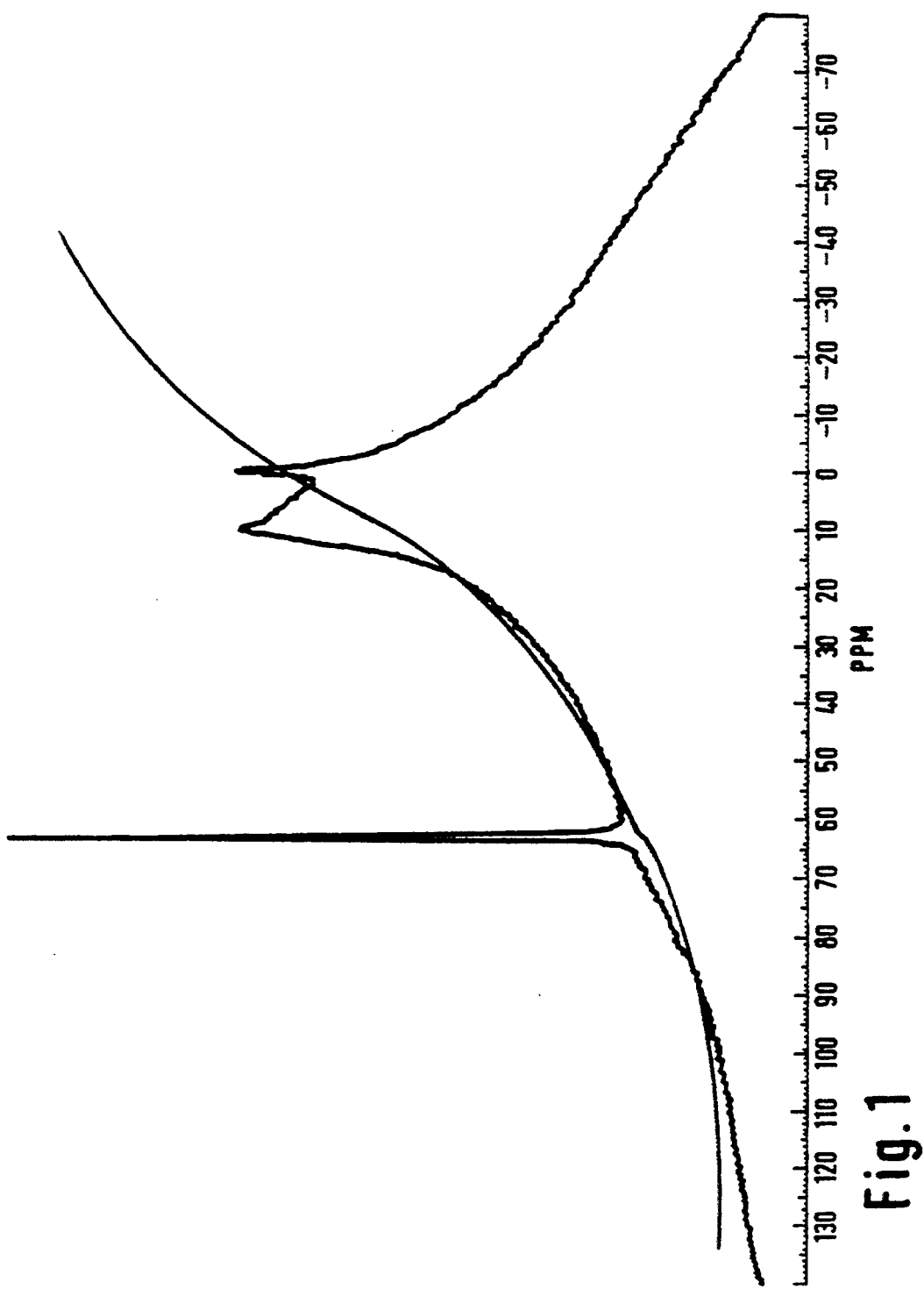

United States Patent [19]

Clarkson

[11] Patent Number: 5,384,112
[45] Date of Patent: Jan. 24, 1995

[54] COMPOUNDS

[75] Inventor: Quinten R. M. Clarkson, Weybridge, England

[73] Assignee: Beecham Group p.l.c., England

[21] Appl. No.: 8,078

[22] Filed: Jan. 22, 1993

Related U.S. Application Data

[63] Continuation of Ser. No. 539,791, Jun. 18, 1990, abandoned, which is a continuation of Ser. No. 169,866, Mar. 17, 1988, abandoned.

[30] Foreign Application Priority Data

Mar. 19, 1987 [GB] United Kingdom ................ 8706583
Aug. 18, 1987 [GB] United Kingdom ................ 8719458
Dec. 15, 1987 [GB] United Kingdom ................ 8729215

[51] Int. Cl.⁶ ............................ A61K 7/38; A61K 9/12; C01B 7/00
[52] U.S. Cl. .............................. 423/462; 424/DIG. 5; 424/47; 424/68
[58] Field of Search ........................... 423/462

[56] References Cited

U.S. PATENT DOCUMENTS 3,920,406 11/1975 Danner et al. ................ 423/462
4,271,138 6/1981 Kennedy et al. ............ 423/462

FOREIGN PATENT DOCUMENTS 0006739 9/1980 European Pat. Off. ........... 423/68
50-5159 2/1975 Japan ......................... 423/462

Primary Examiner—Dale R. Ore
Attorney, Agent, or Firm—Rosenman & Colin

[57] ABSTRACT

A partially neutralized aluminium salt, wherein at least 25% of the total aluminium is present in a form which has a Relative Retention Time (as hereinbefore defined) in the range 0.82 to 0.91 and/or an $^{27}Al$ NMR spectrum wherein 8% to 25% of the total area under the spectrum from 140 ppm to −80 ppm is contained in a peak at approximately 63 ppm, is new and useful as an antiperspirant compound.

4 Claims, 3 Drawing Sheets

COMPOUNDS

This is a continuation of Ser. No. 07/539791 filed Jun. 18, 1990, which is a continuation of Ser. No. 169,866 filed Mar. 17, 1988, both now abandoned.

This invention relates to novel antiperspirant compounds comprising hydroxy aluminium species with a particular molecular size distribution, as well as to processes for their production and their use in antiperspirant compositions.

Known antiperspirant compounds include partially neutralized aluminium and/or zirconium salts such as aluminium chlorhydrate, zirconyl hydroxychloride, and aluminium zirconium tetrachlorhydrate. A particular group of known compounds is the aluminium basic halides of empirical formula $Al_2(OH)_{(6-n)}X_n$ wherein X is a halide and $0<n<6$. The compound wherein X is chloride and n is approximately 1 (more particularly, $0.95 \leq n \leq 1.05$) is known as aluminium chlorhydrate.

Aluminium chlorhydrate is also known to be an antimicrobial agent.

In a previously proposed process, an aluminium or zirconium halide is partially neutralized with an alkali metal hydroxide, aluminium, or zirconium hydroxide, resulting in the formation of a hydroxy-halide compound. Partial neutralization of the strongly acidic halide reduces its irritancy and clothing damage potential. However, it also causes the formation of several species with varying antiperspirant efficacies. The ratios of these species in relation to each other can vary, and as the process can be difficult to control, optimum antiperspirant efficacy is not easily achieved. It is known that increased proportions of the smaller species can be obtained by decreasing the degree of neutralization, but at a cost in terms of the acceptability of the end product.

Methods to adjust the ratios favorably after partial neutralization have been suggested. However, these involve heating the hydroxyhalide for long periods of time, which is work intensive and expensive.

EP-A-O 006 739 describes the use of such a heating step to obtain aluminium chlorhydrate having particular characteristics when assessed by gel permeation chromatography (gpc). Using the gpc procedure described, at least 20% of the aluminium present in the aluminium chlorhydrate was found to be contained in a fraction eluting at Relative Retention Times (RRT) between 0.76 and 0.82 (as opposed to up to 10% in the case of commercially available aluminium chlorhydrate) and the species eluting in this fraction were stated to be associated with enhanced antiperspirant efficacy.

Aluminium chlorhydrate can also be characterized by $^{27}Al$ NMR spectroscopy. FIG. 1 is the $^{27}Al$ NMR spectrum of commercially available aluminium chlorhydrate, in which the underlying broad hump clearly illustrates the presence of large polymeric species.

It has now surprisingly been found that aluminium chlorhydrate can be prepared having an increased proportion of smaller species and virtually free large polymeric species.

A first aspect of the present invention provides a partially neutralized aluminium salt such as the chlorhydrate in which at least 25%, preferably at least 50%, of the total aluminium is present in a form with a Relative Retention Time in the range 0.82 to 0.91, when measured using the procedure described hereinbelow in the Example.

Figure 2:
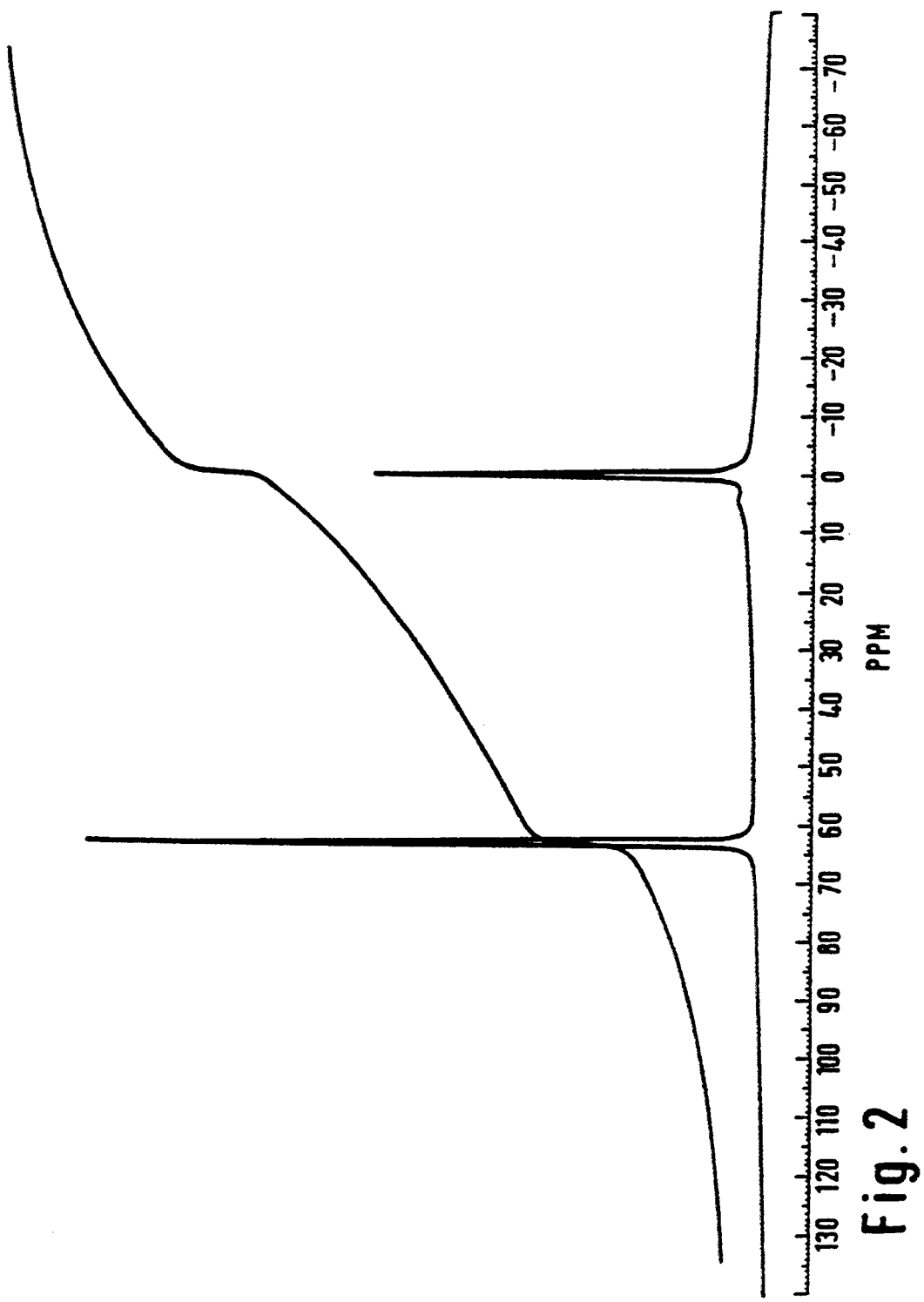
Figure 3:
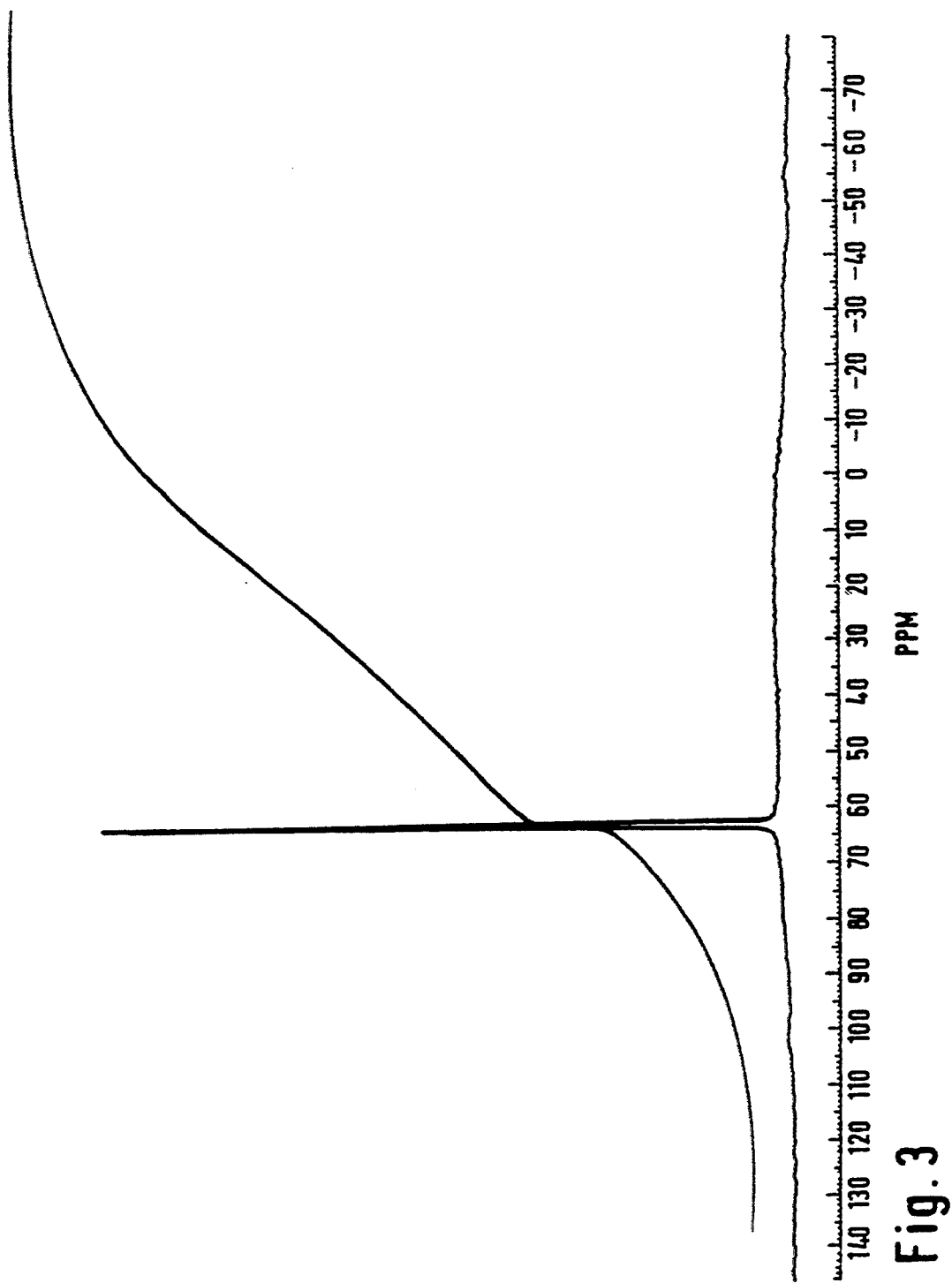

A second aspect of the present invention provides a partially neutralized aluminium salt such as the chlorhydrate in which at least 25%, preferably at least 50%, of the total aluminium is present in a form having an $^{27}Al$ NMR spectrum wherein 8% to 25% of the total area under the spectrum from 140 ppm to $-80$ ppm is contained in a peak at approximately 63 ppm (corresponding to tetrahedrally co-ordinated aluminium ions). More especially the $^{27}Al$ NMR spectrum is substantially as shown in FIG. 2 or 3.

Thus a particularly preferred aspect of the invention provides an antiperspirant compound comprising aluminium halohydrate of the general formula:

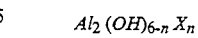

$$Al_2(OH)_{6-n} X_n$$

where $$0.8 < n < 2.0$$

$$X = F, Cl, Br \text{ or } I$$

wherein at least 25%, preferably at least 50%, of the aluminium is present in species that have a Relative Retention Time in the range 0.82 to 0.91 by a gel permeation chromatography method as defined hereinbelow and an $^{27}Al$ NMR spectrum in which 8% to 25% of the total area is beneath the peak occurring at approximately 63 ppm.

The peak at approximately 63 ppm corresponds to the central aluminium ion of $Al_{13}$ complex, and a further aspect of the invention provides a partially neutralized aluminium salt such as the chlorhydrate which consists essentially of this complex. The $^{27}Al$ NMR spectrum of aluminium chlorhydrate consisting essentially of $Al_{13}$ complex is shown in FIG. 3, from which it can be seen that about 10% of the total area under the spectrum from 140 ppm to $-80$ ppm is contained in the peak at approximately 63 ppm.

It is estimated that not more than about 15% of the total aluminium in commercially available aluminium chlorhydrate is present in the form of $Al_{13}$ complex. It will thus be appreciated that the level of $Al_{13}$ complex in commercially available aluminium chlorhydrate could be enhanced by admixture with aluminium chlorhydrate according to the invention.

The present invention further provides a process for the preparation of an antiperspirant compound, which process comprises the partial neutralization of an aqueous acid such as a mineral acid using a source of aluminate ion, as well as a product obtainable by such a process and its use in antiperspirant compositions. No subsequent heating step is required. The mineral acid may be an aluminium and/or zirconium salt which may optionally have already been partially neutralized by other means.

Suitable aluminium and zirconium salts include aluminium halides and nitrate, and zirconium oxyhalides and nitrate. As used herein, 'halide' means fluoride, chloride, bromide or iodide. Particularly suitable aluminium and zirconium halides are aluminium chloride, aluminium bromide and zirconium oxychloride.

Particularly preferred is aluminium chloride. Mixtures of aluminium and/or zirconium salts can be used.

The aluminate ion source may be an organic or inorganic salt and is typically sodium aluminate or potassium aluminate.

Suitably, an aqueous solution of the aluminium or zirconium salt(s) or mixture thereof is used having a total concentration of from 0.1% w/w to 30% w/w, more preferably 5% w/w to 30% w/w.

Advantageously, an aqueous solution of one or more aluminate salts is used having a total concentration of from 0.1% w/w to 10% w/w.

Where the aluminium or zirconium salt has not already been partially neutralized, the molar ratio aluminium and/or zirconium ions: aluminate ions is typically in the range 1:1.86 to 1.64:1, preferably 1:1.86 to 1:1.00, more preferably about 1:1.6 (corresponding to about 82% partial neutralization).

The partial neutralization step is typically carried out at elevated temperatures, more particularly at least 65° C.

After partial neutralization, the product may be processed to remove unwanted by-products such as sodium chloride and then either precipitated and dried by any suitable method including freeze drying, evaporation and spray drying, or prepared as a solution of any required concentration.

In a typical process according to the invention, aqueous solutions of aluminium halide and aluminate are prepared separately. A volume of the halide solution is stirred at the desired temperature. The aluminate solution is then added slowly with rapid stirring. The temperature is maintained throughout the addition. Care is taken to avoid the formation of any precipitate which is visible for more than a few seconds. Neutralization is carried out until a pH of between 1.5 and 6.0, more particularly between 4 and 5, is achieved. The end solution is diluted, pumped through a selectively permeable membrane with a molecular weight cut-off of about 250, and the permeate discarded. The material retained by the membrane may then be dried to a powder. If dried, the product can then be micronized or redissolved or otherwise treated in order to render it suitable for use.

A still further aspect of the invention provides a process for the preparation of a compound of the invention by reverse osmosis, which process comprises pumping a solution of a partially neutralized aluminium salt such as the chlorhydrate through a selectively permeable membrane with a molecular weight cut-off of 500 to 2000, preferably about 1000.

Thus the undesired large polymeric species are retained by the membrane, whilst the permeate, which contains the low molecular weight species, can be further processed, e.g. by drying, as described above.

Typically the solution comprises an aqueous solution having a concentration of 1% w/w to 20% w/w partially neutralized aluminium salt.

Alternatively the solution may be dialysed to remove the large species, by analogy with known dialysis techniques.

The invention further provides a process for the preparation of a compound of the invention, which process comprises subjecting a solution of a partially neutralized aluminium salt such as the chlorhydrate to gel permeation chromatography, collecting one or more fractions, and, optionally, combining two or more of the fractions collected, such that at least 25%, preferably at least 50%, of the aluminium contained in the end product elutes at a Relative Retention Time in the range 0.82 to 0.91 when measured by gpc as described hereinbelow.

A further aspect of the invention provides a method for reducing or preventing perspiration and/or malodour which method comprises applying a compound of the invention to the body surface.

In another aspect the invention provides an antiperspirant composition comprising a compound of the invention and an inert carrier or diluent therefor.

Suitably the composition may be presented in conventional form, for instance as a gel, aerosol, pump pack, tissue, roll-on formulation, cream, lotion or stick, and will contain conventional carriers and diluents known to be suitable for each particular presentation. The composition may also comprise optional accessory ingredients such as additional deodorants, perfume, coloring and preserving agents, antibacterials and antimicrobial agents such as triclosan and chlorhexidine.

Preferably the compositions described above comprise from 2% to 25% w/w of the compound of the invention, more preferably from 10% to 20%.

Particularly preferred accessory ingredients include irritancy reducing compounds such as amino acids, hydroxy acids and urea. These compounds are also gelling inhibitors.

The following Examples illustrate the invention but are not intended to limit the scope of the invention in any way.

EXAMPLE 1

50g 15% w/w aqueous aluminium chloride hexahydrate is heated to 75° C.±5° C. 500g of 1% w/w aqueous sodium aluminate is added over 1 hour with rapid stirring. The temperature is maintained as stated throughout; the final solution has a pH of approximately 3.5. This is dried down to a solid.

EXAMPLE 2

The process of Example 1 was carried out using, instead of 500g, 600g 1% w/w aqueous sodium aluminate, corresponding to 82% partial neutralization, and a pH of 4.1 in the final solution.

BRIEF OF DRAWINGS

FIG. 1 is the $^{27}Al$ nmr spectrum of commercially available aluminium chlorhydrate.

FIG. 2 is the $^{27}Al$ nmr spectrum of aluminium chlorhydrate prepared in accordance with Example 1. The two peaks correspond to octahedral (0 ppm) and tetrahedral (63 ppm) species. The sharpness of the peaks and the absence of an underlying broad hump clearly illustrate the dominance of small molecular species namely $Al^{3+}$ and $Al_{13}$ complex, and the absence of (undesired) large polymeric species. It will be appreciated that broad line nmr will reduce the % area under the 63 ppm peak.

FIG. 3 is the $^{27}Al$ nmr spectrum of aluminium chlorhydrate prepared in accordance with Example 2, and consisting essentially of $Al_{13}$ complex.

Aluminium chlorhydrate prepared according to the present invention was subjected to size exclusion chromatography as follows:

The solution for characterization was obtained from the preparation or by dissolving dried material. The solution contained at least 2.5% w/w aluminium. Typically, the starting solution was evaporated down to 15% w/w concentration of the aluminium chlorhydrate. Gel permeation chromatography was performed on a 25cm×4.6 mm stainless steel-column packed with a silanized silica with a nominal particle size of 5 $\mu m$ and a pore size of 60A. The column is available pre-packed under the name Zorbax TMS. Approximately 2 μl of the solution was injected onto the column by means of a precision microliter syringe. The sample was eluted, using 0.05M potassium chloride brought to pH 3.5 using hydrochloric acid, at a flow rate of 1.0 ml/min using a high pressure pump. The technique is substantially similar to that described in EP-A-O 006 739.

A single peak was obtained corresponding to a relative retention time of 0.88. Under the same conditions, commercially available aluminium chlorhydrate gave two peaks corresponding to relative retention times of 0.72 and 0.80.

Commercial aluminium chlorhydrate was obtained from Wickhen Chemicals (Wickenol CPS 336), Reheis Chemicals (Chlorhydrol Microdry) or Hoescht (Locron P).

Commercial sodium aluminate was obtained from BDH Chemicals Ltd., Broom Rd, Poole, Dorset BH12 4MN.

Nmr spectra were taken with a Bruker WN 250 Fourier transform nmr spectrophotometer at 65 MHz with a $D_2O$ external lock and aluminium nitrate as reference solution.

EXAMPLE 3

| Roll-on | |
|---|---|
| Ingredients | % w/w |
| Glycerine | 2.00 |
| Ethoxylated Fatty Alcohol | 1.00 |
| Hydroxyethyl cellulose | 0.80 |
| Antiperspirant active of Example 1 or 2 | 15.00 |
| Deionised water | 81.20 |
| | 100.00 |

EXAMPLE 4

| Ingredients | % w/w |
|---|---|
| Aerosol Concentrate | |
| Bentone Gel | 35.27 |
| Cyclomethicone | 27.45 |
| Antiperspirant active of Example 1 or 2 | 37.28 |
| | 100.00 |
| Fill | |
| Concentrate | 13.12 |
| Propellent 11 | 54.73 |
| Propellent 12 | 32.15 |
| | 100.00 |

I claim:
1. An aluminum halohydrate of the formula

$$Al_2(OH)_{6-n}X_n$$

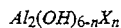

wherein $0.8 \leq n \leq 2.0$ and X is fluorine, chlorine, bromine or iodine, at least 50% of the total aluminum of said aluminum halohydrate being present in a form which has a Relative Retention Time (as hereinbefore defined) in the range 0.82 to 0.91 and which is an $Al_{13}$ complex.

2. A salt according to claim 1, consisting essentially of $Al_{13}$ complex.

3. A salt according to claim 1, having an $^{27}Al$ NMR spectrum as shown in FIG. 2 or FIG. 3 of the accompanying drawings.

4. A process for the preparation of a salt according to claim 1, which process comprises (a) pumping a solution of a partially neutralized aluminium salt through a selectively permeable membrane with a molecular weight cut-off in the range 500 to 2000, or (b) dialysing a said solution to remove species having a molecular weight greater than a selected value within the said range, or (c) subjecting a said solution to gel permeation chromatography, collecting one or more fractions, and optionally, combining two or more of the fractions collected, such that at least 50% of the aluminium contained in the end product has a Relative Retention Time (as hereinbefore defined) in the range 0.82 to 0.91.

* * * * *